United States Patent
Fang et al.

(10) Patent No.: US 7,790,819 B1
(45) Date of Patent: Sep. 7, 2010

(54) BICYCLIC ORGANOSILICON COMPOUNDS AS ELECTRON DONORS FOR POLYOLEFIN CATALYSTS

(75) Inventors: Yiqun Fang, Port Lavaca, TX (US); Honglan Lu, Port Lavaca, TX (US)

(73) Assignee: Formosa Plastics Corporation, U.S.A., Livingston, NJ (US)

( * ) Notice: Subject to any disclaimer, the term of this patent is extended or adjusted under 35 U.S.C. 154(b) by 0 days.

(21) Appl. No.: 12/422,705

(22) Filed: Apr. 13, 2009

(51) Int. Cl.
C08F 4/44 (2006.01)
C08F 4/02 (2006.01)
C07F 9/02 (2006.01)

(52) U.S. Cl. .............. 526/128; 502/121; 502/122; 502/124; 502/125; 526/126; 556/403; 556/404; 556/407; 556/426; 556/483

(58) Field of Classification Search .............. 556/400, 556/402, 403, 404, 407, 426, 430, 482, 483; 502/121, 122, 124, 125; 526/126, 128
See application file for complete search history.

(56) References Cited

U.S. PATENT DOCUMENTS

| | | | |
|---|---|---|---|
| 3,452,072 | A | 6/1969 | Sporck |
| 4,107,414 | A | 8/1978 | Giannini et al. |
| 4,186,107 | A | 1/1980 | Wagner |
| 4,226,963 | A | 10/1980 | Giannini et al. |
| 4,347,160 | A | 8/1982 | Epstein et al. |

(Continued)

FOREIGN PATENT DOCUMENTS

CA 2319786 A1 * 8/1999

(Continued)

OTHER PUBLICATIONS

Knopf, Claudia. Novel Five- and Six-Membered Diazasilacyclalkanes: Synthesis, Structure and Properties. Z. Naturforsch. 59b, 2004. 1337-1347. Aug. 12, 2004.*

(Continued)

*Primary Examiner*—David Wu
*Assistant Examiner*—Elizabeth Eng
(74) *Attorney, Agent, or Firm*—Howrey LLP

(57) ABSTRACT

Cyclic organosilicon compounds that may be employed as an electron donor for polymerization catalyst systems, polymerization catalyst systems employing the cyclic organosilicon compounds as an electron donor, methods of making the polymerization catalyst systems, and polymerization processes to produce polyolefin are disclosed. The organosilicon compounds, which are useful as electron donors in polymerization catalyst systems for the production of polyolefins, are represented by the formula:

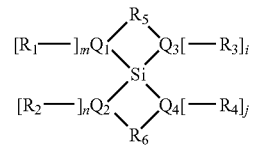

where $Q_1$, $Q_2$, $Q_3$, and $Q_4$ may be identical or different and are each hetero-atoms selected from the group consisting of N, O, S, Si, B, and P. $R_1$, $R_2$, $R_3$, and $R_4$ may be identical or different and are each hydrocarbon-based substituents to $Q_1$, $Q_2$, $Q_3$, and $Q_4$, respectively. The subscripts i, j, m, and n are independently 0 to 3 $R_5$ and $R_6$ may be identical or different and are each a bridging group with a backbone chain length between the two hetero-atoms $Q_1$ and $Q_3$, and $Q_2$ and $Q_4$, respectively, 1-8 atoms. The bridging group is selected from the group consisting of aliphatic, alicyclic, and aromatic bivalent radicals.

21 Claims, 4 Drawing Sheets

GC/MS spectrum of the silane compound made in Example 1A

U.S. PATENT DOCUMENTS

| | | |
|---|---|---|
| 4,382,019 A | 5/1983 | Greco |
| 4,435,550 A | 3/1984 | Ueno et al. |
| 4,465,782 A | 8/1984 | McKenzie |
| 4,472,524 A | 9/1984 | Albizzati |
| 4,473,660 A | 9/1984 | Albizzati et al. |
| 4,522,930 A | 6/1985 | Albizzati et al. |
| 4,530,912 A | 7/1985 | Pullukat et al. |
| 4,532,313 A | 7/1985 | Matlack |
| 4,560,671 A | 12/1985 | Gross et al. |
| 4,581,342 A | 4/1986 | Johnson et al. |
| 4,657,882 A | 4/1987 | Karayannis et al. |
| 5,106,807 A | 4/1992 | Morini et al. |
| 5,208,302 A | 5/1993 | Nakajo et al. |
| 5,407,883 A | 4/1995 | Fushimi et al. |
| 5,684,173 A | 11/1997 | Hosaka et al. |
| 5,773,537 A | 6/1998 | Mueller et al. |
| 5,902,765 A | 5/1999 | Takahashi et al. |
| 5,948,872 A | 9/1999 | Kioka et al. |
| 6,121,483 A | 9/2000 | Fushimi et al. |
| 6,187,883 B1 | 2/2001 | Satoh et al. |
| 6,228,961 B1 | 5/2001 | Grison et al. |
| 6,331,501 B1 | 12/2001 | Satoh et al. |
| 6,362,124 B1 | 3/2002 | Kuribayashi et al. |
| 6,376,628 B1 | 4/2002 | Ikai et al. |
| 6,469,112 B2 | 10/2002 | Cheng et al. |
| 6,552,136 B1 | 4/2003 | Ota et al. |
| 6,689,849 B1 | 2/2004 | Sadashima et al. |
| 6,770,586 B2 | 8/2004 | Tashino et al. |
| 6,800,703 B1 | 10/2004 | Reinking et al. |
| 7,009,015 B2 | 3/2006 | Evain et al. |
| 7,244,794 B2 | 7/2007 | Park et al. |
| 2006/0252894 A1 | 11/2006 | Thorman et al. |

FOREIGN PATENT DOCUMENTS

| | | |
|---|---|---|
| EP | 0959083 A1 | 11/1999 |
| JP | 63245408 A | 10/1988 |
| JP | 02232207 A | 9/1990 |
| JP | 04080207 A | 3/1992 |
| JP | 04080208 A | 3/1992 |
| JP | 04080209 A | 3/1992 |
| JP | 04080210 A | 3/1992 |
| JP | 04175313 A | 6/1992 |
| JP | 04370103 A | 12/1992 |
| JP | 04372609 A | 12/1992 |
| JP | 06128329 A | 5/1994 |
| JP | 2000109513 A | 4/2000 |
| JP | 2000109514 A | 4/2000 |
| JP | 2006028312 A | 2/2006 |
| WO | WO03/014167 A1 | 2/2003 |
| WO | WO 03/014167 A1 | 2/2003 |
| WO | WO 2008/066200 A1 | 6/2008 |
| WO | WO 2008/093953 A1 | 8/2008 |

OTHER PUBLICATIONS

Knopf, Claudia, et al., Novel Five- and Six-Membered Diazasilacycloalkanes: Synthesis, Structure and Properties, Zeitschrift fur Naturforschung, (2004), pp. 1337-1347, vol. 59b, No. 11/12, A Journal of Chemical Sciences, Gegrunder 1946 in den Instituten der Max-Planck-Gesellschaft, Tubingen.

International Search Report dated Jun. 9, 2010 for PCT/US 10/30910.

* cited by examiner

GC/MS spectrum of the silane compound made in Example 1A

1H NMR Spectrum of the silane compound made in Example 1A

GPC Chromatographs of PP made with different external donors.

GPC Chromatographs of PP made with different external donors

BICYCLIC ORGANOSILICON COMPOUNDS AS ELECTRON DONORS FOR POLYOLEFIN CATALYSTS

BACKGROUND

1. Field of the Invention

This invention relates to cyclic organosilicon compounds that may be employed as an electron donor for polymerization catalyst systems, to polymerization catalyst systems employing the cyclic organosilicon compounds as an electron donor, to methods of making the polymerization catalyst systems, and to polymerization processes to produce polyolefins, particularly polypropylene, having broadened molecular weight distribution employing the polymerization catalyst systems.

2. Description of the Related Art

Ziegler-Natta catalyst systems for polyolefin polymerization are well known in the art. Commonly, these systems are composed of a solid Ziegler-Natta catalyst component and a co-catalyst component, usually an organoaluminum compound. To increase the activity and sterospecificity of the catalyst system for the polymerization of α-olefins, electron donating compounds have been widely used (1) as an internal electron donor in the solid Ziegler-Natta catalyst component and/or (2) as an external electron donor to be used in conjunction with the solid Ziegler-Natta catalyst component and the co-catalyst component. Organosilicon compounds are commonly used as external electron donors.

Common internal electron donor compounds, incorporated in the solid Ziegler-Natta catalyst component during preparation of such component include ethers, ketones, amines, alcohols, phenols, phosphines, and silanes. Examples of such internal electron donor compounds and their use as a component of the catalyst system are described in U.S. Pat. Nos. 4,107,414; 4,186,107; 4,226,963; 4,347,160; 4,382,019; 4,435,550; 4,465,782; 4,522,930; 4,530,912; 4,532,313; 4,560,671; 4,657,882; 5,208,302; 5,902,765; 5,948,872; 6,121,483; and 6,770,586.

In the utilization of Ziegler-Natta type catalysts for polymerizations involving propylene or other olefins for which isotacticity is a possibility, it may be desirable to utilize an external electron donor, which may or may not be in addition to the use of an internal electron donor. It is known in the art that external electron donors act as stereoselective control agents to improve isotacticity, i.e., stereoregularity of the resulted polymer products, by selectively poisoning or converting the active site of non-stereoregularity present on the surface of a solid catalyst. Also, it is well known that polymerization activity, as well as stereoregularity and molecular weight distribution of the resulting polymer, depends on the molecular structure of external electron donor employed. Therefore, in order to improve the polymerization process and the properties of the resulting polymer, there has been an effort and desire to develop various external electron donors, particularly various organosilane compounds. Examples of such external electron donors known in the art are organosilicon compounds containing Si—OCOR, Si—OR, or Si—NR$_2$ bonds, having silicon as the central atom, where R is commonly an alkyl, alkenyl, aryl, arylalkyl, or cycloalkyl with 1-20 carbon atoms. Such compounds are described in U.S. Pat. Nos. 4,472,524; 4,473,660; 4,560,671; 4,581,342; 4,657,882; 5,106,807; 5,407,883; 5,684,173; 6,228,961; 6,362,124; 6,552,136; 6,689,849; 7,009,015; and 7,244,794.

WO03014167 uses cyclic organosilicon compounds containing hetero-atom as an external electron donor in a catalyst system to prepare polypropylene with higher melt flow rate (MFR). The silicon is embedded in a ring system, wherein only one hetero-atom is present. The propylene polymer prepared by using organosilane G with purity of 96% as an external electron donor is stated to have a narrow molecular weight distribution. No molecular weight distribution data are presented for the propylene polymers prepared using other pure organosilanes (purity >95%) as external electron donors.

For certain applications, polymers with a wider molecular weight distribution are desirable. Such polymers have a lower melt viscosity at high shear rates. Many polymer fabrication processes operating with high shear rates, such as injection molding, oriented film and thermobonded fibers, could benefit from a lower viscosity product by improving throughput rates and reducing energy costs. Products with higher stiffness, as measured by flexural modulus, are important for injection molded, extruded, and film products, as the fabricated parts can be down-gauged so that less material is needed to maintain product properties. Broad molecular weight distribution is one of the important contributors to achieving high stiffness of polymeric materials. Therefore, it can be advantageous to tailor polymerization catalyst systems to obtain polymers with a wider molecular weight distribution.

Methods are described in JP-A-63-245408, JP-A-2-232207, and JP-A-4-370103 for the preparation of polymers with wide molecular weight distribution obtained by polymerizing propylene in plural numbers of polymerization vessels or by multiple stage polymerizations. However, the disclosed operations are complicated with low production efficiency, and polymer structure and product quality are difficult to control.

There have been continuing efforts to tailor polymerization catalyst systems to enhance resin processability/extrusion characteristics via broadening of polymer molecular weight distribution through utilization of particular types of external electron donor systems. U.S. Pat. No. 6,376,628 teaches bis (perhydroisoquinolino) dimethoxysilane compounds. U.S. Pat. No. 6,800,703 teaches vinyltrimethoxysilane or dicyclohexyldimethoxysilane compounds as external electron donors to produce polypropylene with broad molecular weight distribution. U.S. Patent Application Publication 20060252894 discloses using mixed donor systems comprising different silane compounds to produce polypropylene with broadened molecular weight distribution.

There is a continuing need for developing catalyst systems that can be used to produce polyolefins, particularly polypropylene, with broadened molecular weight distribution. In addition to broadened molecular weight distribution, desired catalyst systems should also offer good polymerization activity and hydrogen response. Furthermore, the catalyst systems should also offer a steady and wide operating window for controlling isotacticity of the resulting polymers based on end user application requirement.

SUMMARY OF THE INVENTION

This invention relates to cyclic organosilicon compounds that may be employed as an electron donor for polymerization catalyst systems, to polymerization catalyst systems employing the cyclic organosilicon compounds as an electron donor, to methods of making the polymerization catalyst systems, and to polymerization processes to produce polyolefins, particularly polypropylene, having broadened molecular weight distribution employing the polymerization catalyst systems.

In accordance with various aspects thereof, the present invention relates to a catalyst system for the polymerization or co-polymerization of alpha-olefin comprising a solid Ziegler-Natta type catalyst component, a co-catalyst component, and an electron donor component comprising at least one cyclic organosilicon compound of the formula:

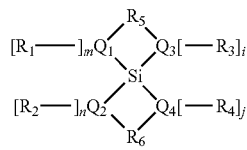

wherein $Q_1$, $Q_2$, $Q_3$ and $Q_4$, which may be identical or different, are each a hetero-atom selected from the group consisting of N, O, S, Si, B, P; wherein $R_1$, $R_2$, $R_3$ and $R_4$, which may be identical or different, are each a hydrocarbon-based substituent to $Q_1$, $Q_2$, $Q_3$ and $Q_4$, respectively; wherein i, j, m, and n are independently 0-3; and wherein $R_5$ and $R_6$, which may be identical or different, are each a bridging group with backbone chain length between their two respective hetero-atoms $Q_1$ and $Q_3$, and $Q_2$ and $Q_4$, respectively, being 1-8 atoms, wherein the backbone of said bridging group are independently selected from the group consisting of aliphatic, alicyclic and aromatic radicals. The present invention also relates to a composition containing a compound of the cyclic organosilicon compound of the aforementioned formula. In accordance with various aspects thereof, the present invention also relates to a method of polymerizing an alpha-olefin comprising polymerizing the alpha-olefin in the presence of the cyclic organosilicon compound of the aforementioned formula.

The features and advantages of the present invention will be readily apparent to those skilled in the art. While numerous changes may be made by those skilled in the art, such changes are within the spirit of the invention.

DESCRIPTION OF PREFERRED EMBODIMENTS

Figure 1:
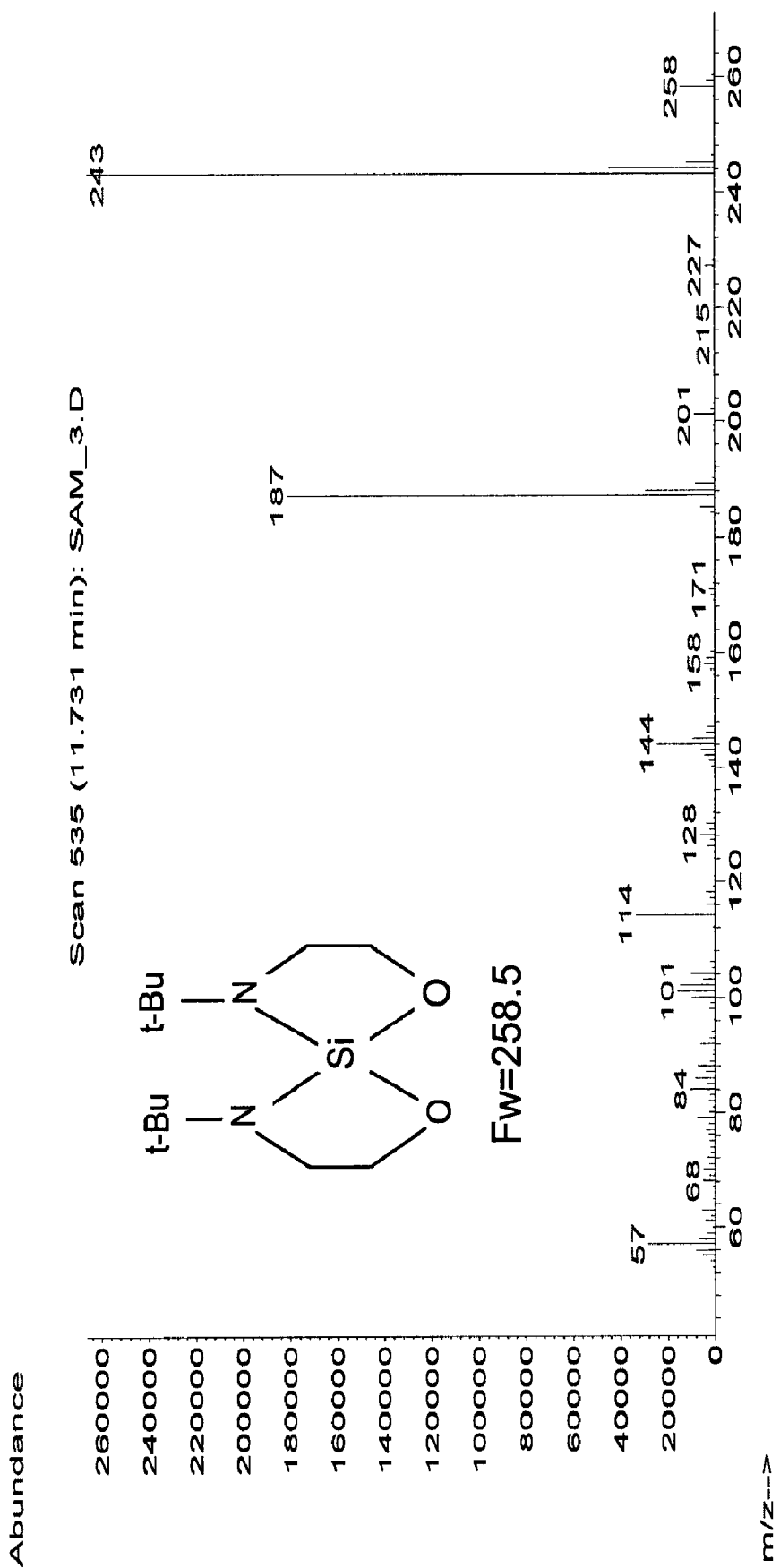
FIG. 1 shows the mass spectrum of the product obtained in accordance with the procedures of Example 1A.

This invention relates to cyclic organosilicon compounds that may be employed as an electron donor for polymerization catalyst systems, to polymerization catalyst systems employing the cyclic organosilicon compounds as an electron donor, to methods of making the polymerization catalyst systems, and to polymerization processes to produce polyolefins, particularly polypropylene, having broadened molecular weight distribution employing the polymerization catalyst systems.

In accordance with various embodiments, a class of organosilicon compounds, which are useful as electron donors in polymerization catalyst systems for the production of polyolefins, particularly polypropylene, are disclosed. These organosilicon compounds may be used as either an internal electron donor or an external electron donor. Preferably, these organosilicon compounds are used as an external electron donor. Polymerization catalyst systems employing the cyclic organosilicon compounds of the present invention may have an internal electron donor, an external electron donor, or both an internal electron donor and an external electron donor.

The organosilicon compounds of the present invention may be used alone as a single constituent in an electron donor component of the catalyst system or may be used in combination with one or more other compounds as an electron donor component of the catalyst system. If more than one compound is used as the electron donor component, one or more of the constituents may be organosilicon compounds of the present invention.

The organosilicon compounds of the present invention that may be used as electron donors in polymerization catalyst systems are represented by Formula 1:

Formula 1

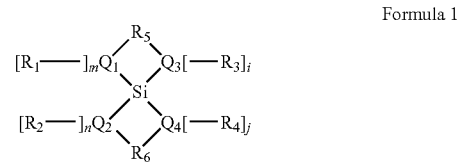

$Q_1$, $Q_2$, $Q_3$, and $Q_4$ may be identical or different and are each hetero-atoms selected from the group consisting of N, O, S, Si, B, and P. In preferred embodiments of the present invention, said $Q_1$ and $Q_2$ in Formula 1, which may be identical or different, are selected from N, O, Si, or B. In preferred embodiments of the present invention, said $Q_3$ and $Q_4$ in Formula 1, which may be identical or different, are selected from N or O.

$R_1$, $R_2$, $R_3$, and $R_4$ may be identical or different and are each hydrocarbon-based substituents to $Q_1$, $Q_2$, $Q_3$, and $Q_4$, respectively. The subscripts i, j, m, and n are independently 0 to 3, which one of ordinary skill in the art having the benefit of this disclosure will recognize will depend on the valency state of $Q_1$, $Q_2$, $Q_3$, and $Q_4$. The length and structure of the $R_1$, $R_2$, $R_3$, and $R_4$ groups are not generally limited. In preferred embodiments of the present invention, said $R_3$ and $R_4$ are small groups, such as hydrogen, methyl, or ethyl. In preferred embodiments of the present invention, at least one of said $R_1$ and $R_2$ is a larger group such as iso-propyl, iso-butyl, and t-butyl.

$R_5$ and $R_6$ may be identical or different and are each a bridging group with a backbone chain length between the two hetero-atoms $Q_1$ and $Q_3$, and $Q_2$ and $Q_4$, respectively, being from 1-8 atoms. "Backbone chain length" in this context refers to the atoms that are in the direct linkage between the two hetero-atoms $Q_1$ and $Q_3$, and $Q_2$ and $Q_4$, respectively. For example, if —$CH_2$— or —$CH_2$—$CH_2$— is the bridging group then the associated backbone chain length is one and two atoms, respectively, referring to the carbon atoms that provide the direct linkage between the two hetero-atoms. Similarly, if the bridging group has the iso-structure, $CH_3CHCH_2$, then the associated backbone chain length is also two atoms.

The backbone of the bridging group is selected from the group consisting of aliphatic, alicyclic, and aromatic radicals. Preferably, the backbone of the bridging group is selected from the group consisting of aliphatic radicals, with or without unsaturation. The bridging group may have one or more $C_1$-$C_{20}$ substituents (or side chains) extending off the backbone chain. The substituents may be branched or linear and may be saturated or unsaturated. Similarly, the substituents may comprise aliphatic, alicyclic, and/or aromatic radicals.

One or more carbon atoms and/or hydrogen atoms of $R_1$, $R_2$, $R_3$, $R_4$ and the bridging groups $R_5$ and $R_6$, including any substituents thereof, may be replaced by a hetero-atom selected from the group consisting of N, O, S, Si, B, P, and halogen atoms.

In various embodiments of the present invention, two or more of said $R_1$, $R_2$, $R_3$, $R_4$, bridging group $R_5$, and bridging group $R_6$ may be linked to form one or more saturated or unsaturated monocyclic or polycylic rings.

In preferred embodiments of the present invention, one or both of said $R_5$ and $R_6$ in Formula 1, which may be identical or different, are bridging groups with backbone chain length between two hetero-atoms $Q_1$ and $Q_3$, or $Q_2$ and $Q_4$, respectively, being from 2 to 4 atoms.

Examples of suitable ring structure organosilicon compounds of the Formula 1 include, but not are limited to:

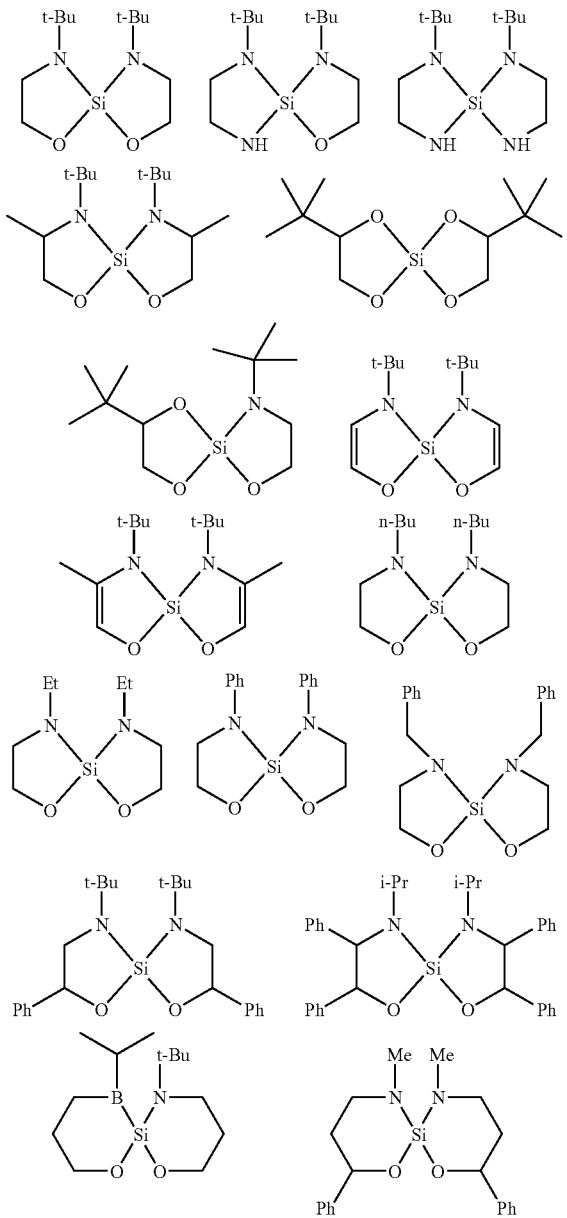

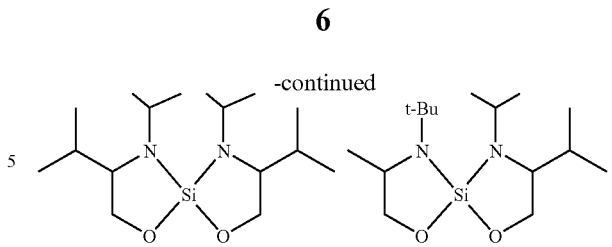

-continued

Examples of suitable ring structure organosilicon compounds of the Formula 1 where two or more of said $R_1$, $R_2$, $R_3$, $R_4$, bridging group $R_5$, and bridging group $R_6$ are linked to form one or more saturated or unsaturated monocyclic or polycylic rings include, but are not limited to:

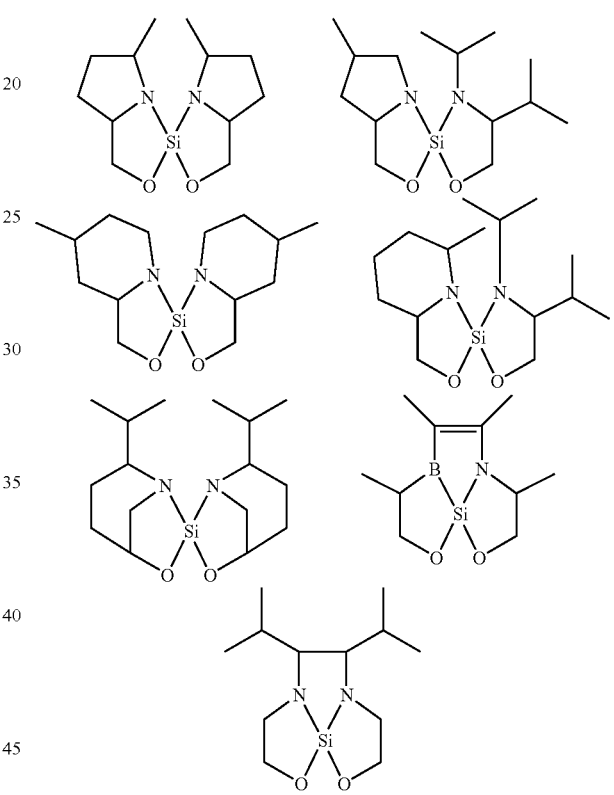

The organosilicon compounds of the present invention are used as a component in Ziegler-Natta type catalyst systems. Except for the inclusion of the organosilicon compounds of the present invention, the Ziegler-Natta type catalyst systems, and methods for making such catalyst systems, which can be employed in accordance with the various embodiments of the present invention, are not generally limited. Typical, and acceptable, Ziegler-Natta type catalyst systems that can be used in accordance with the present invention comprise (a) a solid Ziegler-Natta type catalyst component and (b) a co-catalyst component. In accordance with the various embodiments of the present invention, at least one organosilicon compound in accordance with the present invention is used as an electron donor in the Ziegler-Natta type catalyst system. As previously disclosed herein, these organosilicon compounds may be used as either an internal electron donor or an external electron donor. Preferably, these organosilicon compounds are used as (c) an external electron donor.

Preferred solid Ziegler-Natta type catalyst component (a) include solid catalyst components comprising a titanium compound having at least a Ti-halogen bond and an internal electron donor compound supported on an anhydrous magnesium-dihalide support. Such preferred solid Ziegler-Natta type catalyst component (a) include solid catalyst components comprising a titanium tetrahalide. A preferred titanium tetrahalide is $TiCl_4$. Alkoxy halides may also be used.

Acceptable internal electron donor compounds for the preparing solid Ziegler-Natta type catalyst component (a) are not generally limited and include, but are not limited to, alkyl, aryl, and cycloalkyl esters of aromatic acids, in particular the alkyl esters of benzoic acid and phthalic acid and their derivatives. Examples of such compounds include ethyl benzoate, n-butyl benzoate, methyl-p-toluate, methyl-p-methoxybenzoate, and diisobutylphthalate. Other common internal electron donors, including alkyl or alkyl-aryl ethers, ketones, mono- or polyamines, aldehydes, and P-compounds, such as phosphines and phosphoramides, can also be used. Finally, the organosilicon compounds of the present invention may also be employed as an internal electronic donor.

Acceptable anhydrous magnesium dihalides forming the support of the solid Ziegler-Natta type catalyst component (a) are the magnesium dihalides in active form that are well known in the art. Such magnesium dihalides may be preactivated, may be activated in situ during the titanation, may be formed in-situ from a magnesium compound, which is capable of forming magnesium dihalide when treated with a suitable halogen-containing transition metal compound, and then activated. Preferred magnesium dihalides are magnesium dichloride and magnesium dibromide. The water content of the dihalides is generally less than 1% by weight.

The solid Ziegler-Natta type catalyst component (a) can be made by various methods. One such method consists of co-grinding the magnesium dihalide and the internal electron donor compound until the product shows a surface area higher than 20 $m^2$/g and thereafter reacting the ground product with the Ti compound. Other methods of preparing solid Ziegler-Natta type catalyst component (a) are disclosed in U.S. Pat. Nos. 4,220,554; 4,294,721; 4,315,835; 4,330,649; 4,439,540; 4,816,433; and 4,978,648. These methods are incorporated herein by reference.

In a typical solid Ziegler-Natta type catalyst component (a), the molar ratio between the magnesium dihalide and the halogenated titanium compound is between 1 and 500 and the molar ratio between said halogenated titanium compound and the internal electron donor is between 0.1 and 50.

Preferred co-catalyst component (b) includes aluminum alkyl compounds. Acceptable aluminum alkyl compounds include aluminum trialkyls, such as aluminum triethyl, aluminum triisobutyl, and aluminum triisopropyl. Other acceptable aluminum alkyl compounds include aluminum-dialkyl hydrides, such as aluminum-diethyl hydrides. Other acceptable co-catalyst component (b) includes compounds containing two or more aluminum atoms linked to each other through hetero-atoms, such as:

$(C_2H_5)_2Al$—O—$Al(C_2H_5)_2$
$(C_2H_5)_2Al$—$N(C_6H_5)$—$Al(C_2H_5)_2$; and
$(C_2H_5)_2Al$—O—$SO_2$—O—$Al(C_2H_5)_2$.

The olefin polymerization processes that can be used in accordance with the present invention are not generally limited. For example, the catalyst components (a), (b) and (c), when employed, can be added to the polymerization reactor simultaneously or sequentially. It is preferred to mix components (b) and (c) first and then contact the resultant mixture with component (a) prior to the polymerization.

The olefin monomer can be added prior to, with, or after the addition of the Ziegler-Natta type catalyst system to the polymerization reactor. It is preferred to add the olefin monomer after the addition of the Ziegler-Natta type catalyst system.

The molecular weight of the polymers may be controlled by known methods, preferably by using hydrogen. With the catalysts produced according to the present invention, molecular weight may be suitably controlled with hydrogen when the polymerization is carried out at relatively low temperatures, e.g., from about 30° C. to about 105° C. This control of molecular weight may be evidenced by a measurable positive change of the Melt Flow Rate (MFR).

The polymerization reactions can be carried out in slurry, liquid or gas phase processes, or in a combination of liquid and gas phase processes using separate reactors, all of which can be done either by batch or continuously. The polyolefin may be directly obtained from gas phase process, or obtained by isolation and recovery of solvent from the slurry process, according to conventionally known methods.

There are no particular restrictions on the polymerization conditions for production of polyolefins by the method of the invention, such as the polymerization temperature, polymerization time, polymerization pressure, monomer concentration, etc. The polymerization temperature is generally from 40-90° C. and the polymerization pressure is generally 1 atmosphere or higher.

The Ziegler-Natta type catalyst systems of the present invention may be precontacted with small quantities of olefin monomer, well known in the art as prepolymerization, in a hydrocarbon solvent at a temperature of 60° C. or lower for a time sufficient to produce a quantity of polymer from 0.5 to 3 times the weight of the catalyst. If such a prepolymerization is done in liquid or gaseous monomer, the quantity of resultant polymer is generally up to 1000 times the catalyst weight.

The Ziegler-Natta type catalyst systems of the present invention are useful in the polymerization of olefins, including but not limited to homopolymerization and copolymerization of alpha olefins. Suitable α-olefins that may be used in a polymerization process in accordance with the present invention include olefins of the general formula $CH_2$=CHR, where R is H or $C_{1-10}$ straight or branched alkyl, such as ethylene, propylene, butene-1, pentene-1, 4-methylpentene-1 and octene-1. While the Ziegler-Natta type catalyst systems of the present invention can be employed in processes in which ethylene is polymerized, it is more desirable to employ the Ziegler-Natta type catalyst systems of the present invention in processes in which polypropylene or higher olefins are polymerized. Processes involving the homopolymerization or copolymerization of propylene are preferred.

To facilitate a better understanding of the present invention, the following examples of certain aspects of some embodiments are given. In no way should the following examples be read to limit, or define, the entire scope of the invention.

EXAMPLES

The catalyst components and properties of polymers in the examples were measured according to the following methods:

$^1$H-NMR and GC/MS were used to characterize the organosilane compounds.

Organosilicon compounds analyses were conducted by GC/MS (Gas Chromatograph with Mass Spectrometry) with Chemstation software G1701BA version B.01.00 for data handling.

Instruments used in analyses are listed as follows:

Gas Chromatography: Agilent 5890 Series II Plus
Injector: Agilent 7673 Auto Injector
Mass Spectra Detector: Agilent 5989B
The Column was a Phenomenex ZB-5ms 5% Polysilarylene and 95% Polydimethylsiloxane with dimensions of 30 meters length, 0.25 mm ID, and 1.00 micron film thickness. The chromatographic conditions were as follows: GC inlet temperature 250° C.; oven temperature program set 50° C. initially, to 130° C. at 35° C. per minute, and to 320° C. at 12° C. per minute and held for 6 minutes; column flow rate of 1.0 ml/min; a split flow rate of 1:75; injection volume of 1.0 micro liter; and mass spectra scan range 50-650 amu. The mass spectra were obtained from the TIC mode (total ion chromatogram) after GC separation.

The following analytical methods were used to characterize the polymer.

Heptane Insolubles (HI): The residuals of PP after extracted with boiling heptane for 6 hours.

Melt Flow Rate: ASTM D-1238, determined at 230° C., under the load of 2.16 kg.

Tm: ASTM D-3417, determined by DSC (Manufacturer: TA Instrument, Inc.; Model: DSC Q1000).

Molecular weight (Mn and Mw): The weight average molecular weight (Mw), number average molecular weight (Mn), and molecular weight distribution (Mw/Mn) of polymers were obtained by gel permeation chromatography on Waters 2000GPCV system using Polymer Labs Plgel 10 um MIXED-B LS 300×7.5 mm columns and 1,2,4,4-trichlorobenzene (TCB) as mobile phase. The mobile phase was set at 0.9 ml/min, and temperature was set at 145° C. Polymer samples were heated at 150° C. for two hours . Injection volume was 200 microliters. External standard calibration of polystyrene standards was used to calculate the molecular weight.

Specimens for below tests were injection molded according to the conditions specified in ASTM D-4101.
Flexural Modulus (1.3mm/min), 1% Secant: ASTM D-790.
Tensile strength at yield (50mm/min): ASTM D-638.
Elongation at yield (50mm/min): ASTM D-638
Notched IZOD Impact strength @ 73° F.: ASTM D-256.
HDT@66psi: ASTM D-648.
Rockwell Hardness: ASTM D-785

Unless otherwise indicated, all reactions were conducted under an inert atmosphere.

ORGANOSILICON COMPOUND PREPARATION

Example 1A

This example illustrates an organosilicon compound in accordance with the present invention and a method of preparing the same.

Preparation of 4,9-Di-tert-butyl-1,6-dioxa-4,9-diaza-5-sila-spiro[4.4]nonane.

2-(tert-Butylamino)ethanol (0.08 mol, 99%, from Aldrich) was dissolved in THF(100 ml, anhydrous, from Aldrich) in a 250 ml flask with an ice-water bath, and while stirring n-butyllithium (100 ml of a 1.6 M solution in hexanes, from Aldrich) was added dropwise over a period of about 30 minutes. Then, the ice-water bath was removed and the reaction mixture was kept stirring for 20 minutes at room temperature.

Figure 2:
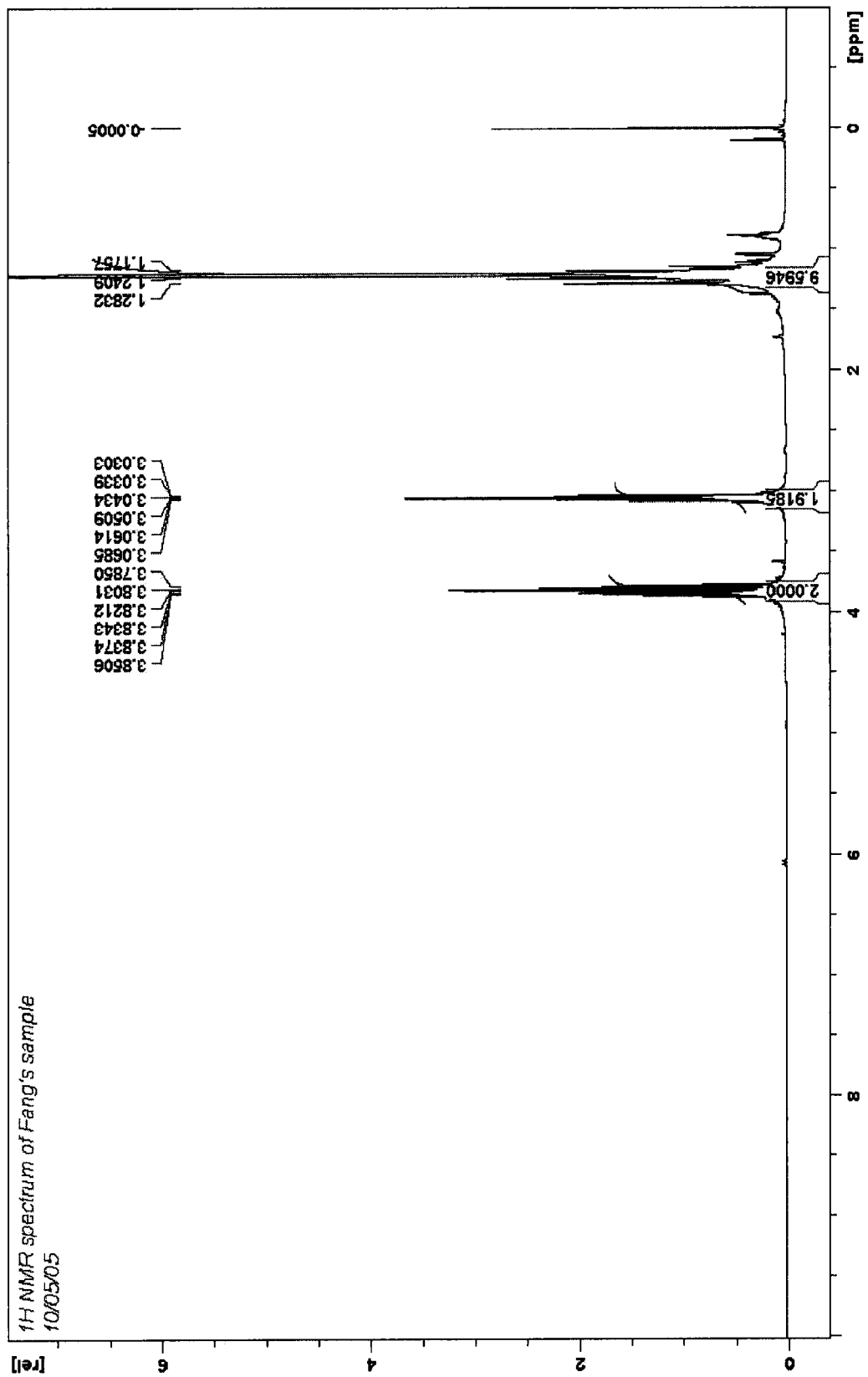
FIG. 2 shows the $^1$H-NMR spectrum of the product obtained in accordance with the procedures of Example 1A.

While stirring, into a 500 ml flask containing 100 ml heptane (Anhydrous, from Aldrich) cooled by an ice-bath, the above prepared reaction mixture and $SiCl_4$(0.04 mol, 99%, from Aldrich) dissolved in 100 ml heptane were added respectively at same time over a period of about 60 minutes and the resultant reaction mixture was stirred for another 30 minutes. Then, the ice-bath was removed and the resultant reaction mixture was stirred at room temperature for 6 hours. Then, the stirring was stopped and the resultant reaction mixture was kept still overnight to precipitate the solid byproduct. The supernatant clear solution was transferred into a flask and condensed under reduced pressure to remove the solvent constituents, such as THF, and subsequently dissolved in melted paraffin wax and distilled and purified to restore the target product. The target product was a liquid with colorless transparent appearance, which had a GC purity of 97%. The target product was identified by gas-mass chromatography, of which mass spectrum is shown in FIG. 1, and $^1$H-NMR is shown in FIG. 2.

Example 1B

This example illustrates another method of preparing 4,9-Di-tert-butyl-1,6-dioxa-4,9-diaza-5-sila-spiro[4.4]nonane.

Preparation of 4,9-Di-tert-butyl-1,6-dioxa-4,9-diaza-5-sila-spiro[4.4]nonane.

2-(tert-Butylamino)ethanol (0.125 mol, 99%, from Aldrich) was dissolved in THF(100ml, anhydrous, from Aldrich) in a 250 ml flask with a ice-water bath, and while stirring n-butyllithium (100 ml of a 2.5 M solution in hexanes, from Aldrich) was added dropwise over a period of about 30 minutes. Then, the ice-water bath was removed and the reaction mixture was stirred for 20 minutes at room temperature.

The above prepared reaction mixture was added into a 500 ml flask containing a stirring mixture of 9.5 g tetramethyl orthosilicate (99%, from Aldrich), 120 ml heptane and 120 ml THF over a period of 5 minutes at room temperature. Thereafter, the reaction temperature was raised to 50° C. with an oil-bath. The reaction was carried out at 50° C. for 5 hours under stirring. Then the stirring was stop, and the resultant reaction mixture was kept still at room temperature overnight to precipitate the solid byproduct. The supernatant clear solution was transferred into a flask and condensed under reduced pressure to remove the solvent constituents, such as THF, and subsequently dissolved in melted paraffin wax and distilled and purified to restore the target product. The target product was a liquid with colorless transparent appearance, which has a GC purity of 97%.

Examples 2 to 8

The procedure and ingredients of Example 1A were repeated except that 2-(tert-Butylamino) ethanol was replaced by the chemicals [$RNH—(CR^1R^2)_n—OH$] shown in Table 1.

TABLE 1

| Example | $RNH—(CR^1R^2)_n—OH$ | Final Product |
|---|---|---|
| 2 | 2-(Butylamino)ethanol | 4,9-Dibutyl-1,6-dioxa-4,9-diaza-5-sila-spiro[4.4]nonane |
| 3 | 2-(Ethylamino)ethanol | 4,9-Diethyl-1,6-dioxa-4,9-diaza-5-sila-spiro[4.4]nonane |
| 4 | N-Phenylethanolamine | 4,9-Diphenyl-1,6-dioxa-4,9-diaza-5-sila-spiro[4.4]nonane |
| 5 | N-Benzylethanolamine | 4,9-Dibenzyl-1,6-dioxa-4,9-diaza-5-sila-spiro[4.4]nonane |

TABLE 1-continued

| Example | RNH—(CR$^1$R$^2$)$_n$—OH | Final Product |
|---|---|---|
| 6 | α-[2-(Methylamino)ethyl]benzyl alcohol | 5,11-Dimethyl-2,8-diphenyl-1,7-dioxa-5,11-diaza-6-sila-spiro[5.5]undecane |
| 7 | (R)-(−)-2-tert-Butylamino-1-phenylethanol | 4,9-Di-tert-butyl-2,7-diphenyl-1,6-dioxa-4,9-diaza-5-sila-spiro[4.4]nonane |
| 8 | 2-(Isopropylamino)-1,2-diphenylethanol | 4,9-Diisopropyl-2,3,7,8-tetraphenyl-1,6-dioxa-4,9-diaza-5-sila-spiro[4.4]nonane |

POLYMERIZATION EXAMPLES

Example 9A

A bench scale 2-liter reactor was used. The reactor was first preheated to at least 100° C. with a nitrogen purge to remove residual moisture and oxygen. The reactor was thereafter cooled to 50° C.

Under nitrogen, 1 liter dry hexane was introduced into the reactor. When the reactor temperature was about 50° C., 2.5 ml triethyl aluminum hexane solution (1.0 M), 0.8 ml 4,9-Di-tert-butyl-1,6-dioxa-4,9-diaza-5-sila-spiro[4.4]nonane heptane solution (0.25M) and then 30 mg Toho 53-009 catalyst (available from Toho Catalyst Ltd.) were added to the reactor. Stirring was started and the pressure of the reactor was raised to 28.5 psig at 50° C. by introducing nitrogen, 8 psig. Hydrogen in a 150 cc vessel was flushed into the reactor with propylene.

The reactor temperature was then raised to 70° C. The total reactor pressure was raised to and controlled at 90 psig by continually introducing propylene into the reactor and the polymerization was allowed to proceed for 1 hour. After polymerization, the reactor was vented to reduce the pressure to 0 psig, and the reactor temperature was cooled down to 50° C.

The reactor was then opened. 500 ml methanol was added to the reactor and the resulting mixture was stirred for 5 minutes and then filtered to obtain the polymer product. The obtained polymer was vacuum dried at 80° C. for 6 hours. The polymer was evaluated for melt flow rate (MFR), percent heptane insolubles (%HI), molecular weight distribution (Mw/Mn). The activity of catalyst (AC) was also measured. The results are shown below in Table 2.

Example 9B

The polymerization was performed in the same manner as in Example 9A except that the amount of 4,9-Di-tert-butyl-1,6-dioxa-4,9-diaza-5-sila-spiro[4.4]nonane (0.25M in heptane) was changed to 1.6 ml. The results are shown below in Table 2.

Example 9C

The polymerization was performed in the same manner as in Example 9A except that the amount of 4,9-Di-tert-butyl-1,6-dioxa-4,9-diaza-5-sila-spiro[4.4]nonane (0.25M in heptane) was changed to 3.2ml. The results are shown below in Table 2.

Comparative Example 1

Figure 3:
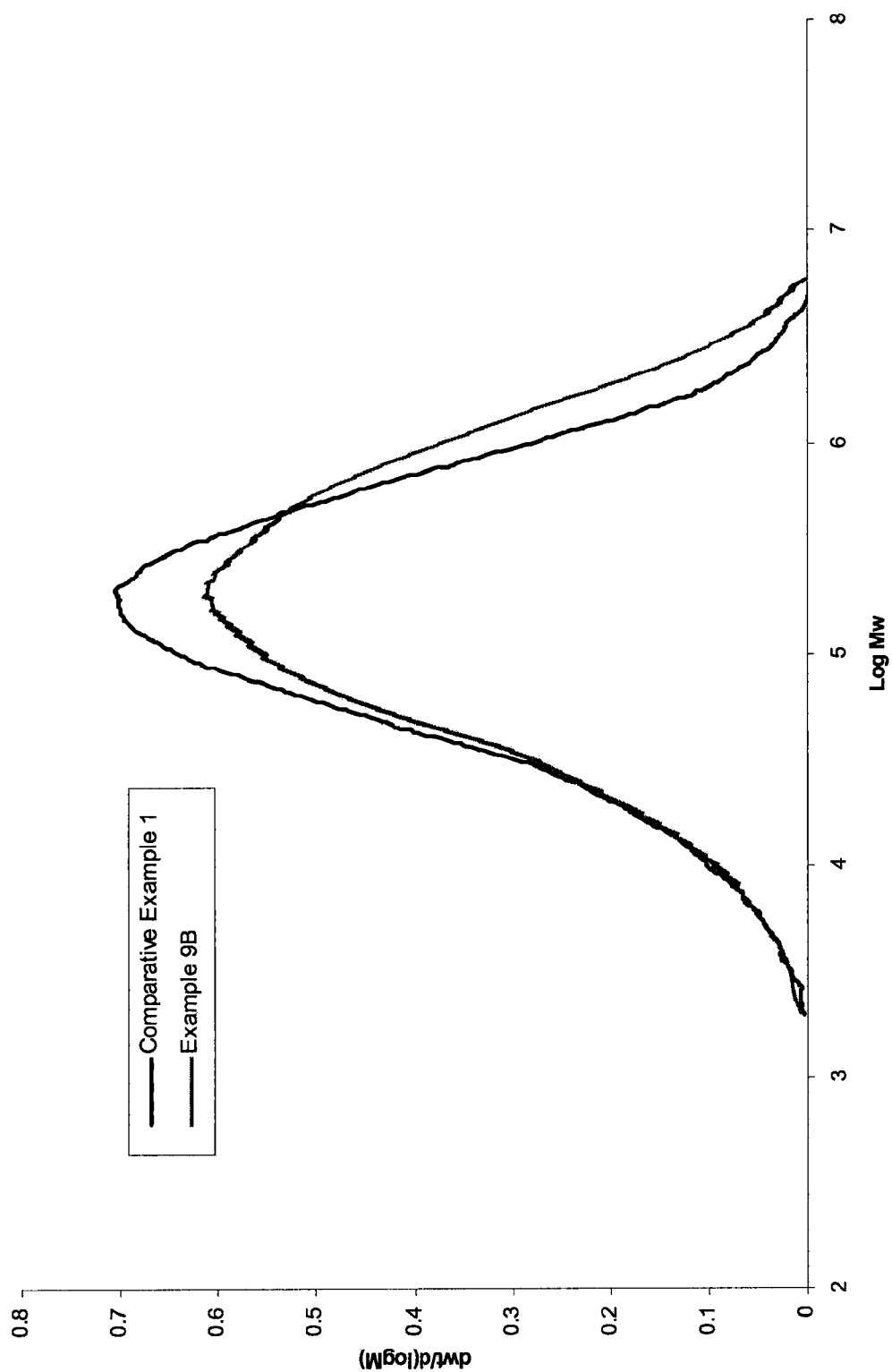
FIG. 3 shows the GPC chromatographs of products obtained in accordance with the procedures of Example 9B and Comparative Example 1.

The polymerization were performed in the same manner as in Example 9A except that the silane 4,9-Di-tert-butyl-1,6-dioxa-4,9-diaza-5-sila-spiro[4.4]nonane was replaced by isobutylisopropyldimethoxysilane(IBIP). The results are shown in Table 2 and FIG. 3.

TABLE 2

| Example | Organosilicon compounds (0.25M) | AC (gPP/gCat · h) | MFR (g/10 min) | HI (%) | Mw/Mn |
|---|---|---|---|---|---|
| Ex. 9A | 4,9-Di-tert-butyl-1,6-dioxa-4,9-diaza-5-sila-spiro[4.4]nonane (0.8 ml) | 4680 | 1.6 | 95.9 | 6.3 |
| Ex. 9B | 4,9-Di-tert-butyl-1,6-dioxa-4,9-diaza-5-sila-spiro[4.4]nonane (1.6 ml) | 4532 | 1.5 | 96.7 | 6.8 |
| Ex. 9C | 4,9-Di-tert-butyl-1,6-dioxa-4,9-diaza-5-sila-spiro[4.4]nonane (3.2 ml) | 3831 | 1.0 | 97.2 | 6.7 |
| Comp. Ex. 1 | IBIP (0.8 ml) | 4650 | 3.4 | 97.8 | 4.8 |

Examples 10 to 16

The polymerization were performed in the same manner as in Example 9A except that 4,9-Di-tert-butyl-1,6-dioxa-4,9-diaza-5-sila-spiro[4.4]nonane was replaced by the organosilicon compounds as shown in Table 1. The results are shown below in Table 3.

TABLE 3

| Example | Organosilicon compounds | AC (gPP/gCat · h) | MFR (g/10 min) | HI (%) | Mw/Mn |
|---|---|---|---|---|---|
| Ex. 10 | 4,9-Dibutyl-1,6-dioxa-4,9-diaza-5-sila-spiro[4.4]nonane | 1675 | 3.4 | 93.9 | 6.3 |
| Ex. 11 | 4,9-Diethyl-1,6-dioxa-4,9-diaza-5-sila-spiro[4.4]nonane | 953 | 2.7 | 93.5 | 6.3 |
| Ex. 12 | 4,9-Diphenyl-1,6-dioxa-4,9-diaza-5-sila-spiro[4.4]nonane | 1063 | 2.4 | 92.4 | 6.1 |
| Ex. 13 | 4,9-Dibenzyl-1,6-dioxa-4,9-diaza-5-sila-spiro[4.4]nonane | 1207 | 2.4 | 91.7 | 6.3 |

TABLE 3-continued

| Example | Organosilicon compounds | AC (gPP/gCat · h) | MFR (g/10 min) | HI (%) | Mw/Mn |
|---|---|---|---|---|---|
| Ex. 14 | 5,11-Dimethyl-2,8-diphenyl-1,7-dioxa-5,11-diaza-6-sila-spiro[5.5]undecane | 1430 | 2.8 | 92.6 | 6.5 |
| Ex. 15 | 4,9-Di-tert-butyl-2,7-diphenyl-1,6-dioxa-4,9-diaza-5-sila-spiro[4.4]nonane | 2363 | 3.2 | 92.1 | 6.1 |
| Ex. 16 | 4,9-Diisopropyl-2,3,7,8-tetraphenyl-1,6-dioxa-4,9-diaza-5-sila-spiro[4.4]nonane | 1146 | 2.65 | 93.1 | 6.2 |

Example 17

A 10-liter reactor was used. The reactor was purged with nitrogen at 90° C. for 1 hour and then cooled down to 30° C. The reactor was vacuumed to remove nitrogen. Then 3.6 kg propylene, 20.2 liter hydrogen, 50 ml triethyl aluminum hexane solution (0.6 M) and 4.5 ml 4,9-Di-tert-butyl-1,6-dioxa-4,9-diaza-5-sila-spiro[4.4]nonane heptane solution (0.5 M) were fed into the 10-liter reactor. Stirring was started. Thereafter, 60 mg Lynx 1010 catalyst (available from BASF Catalyst LLC) in a tube connected to the 10-liter reactor was flushed into the reactor with 0.2 kg liquid propylene. The prepolymerization was carried out at 30° C. for 15 minutes. Then, the temperature was raised to 80° C. over a period of 10 minutes, and the polymerization was run at this temperature for 1 hour. After polymerization, unreacted propylene was vented out, and the temperature of the reactor was lowered to room temperature.

Figure 4:
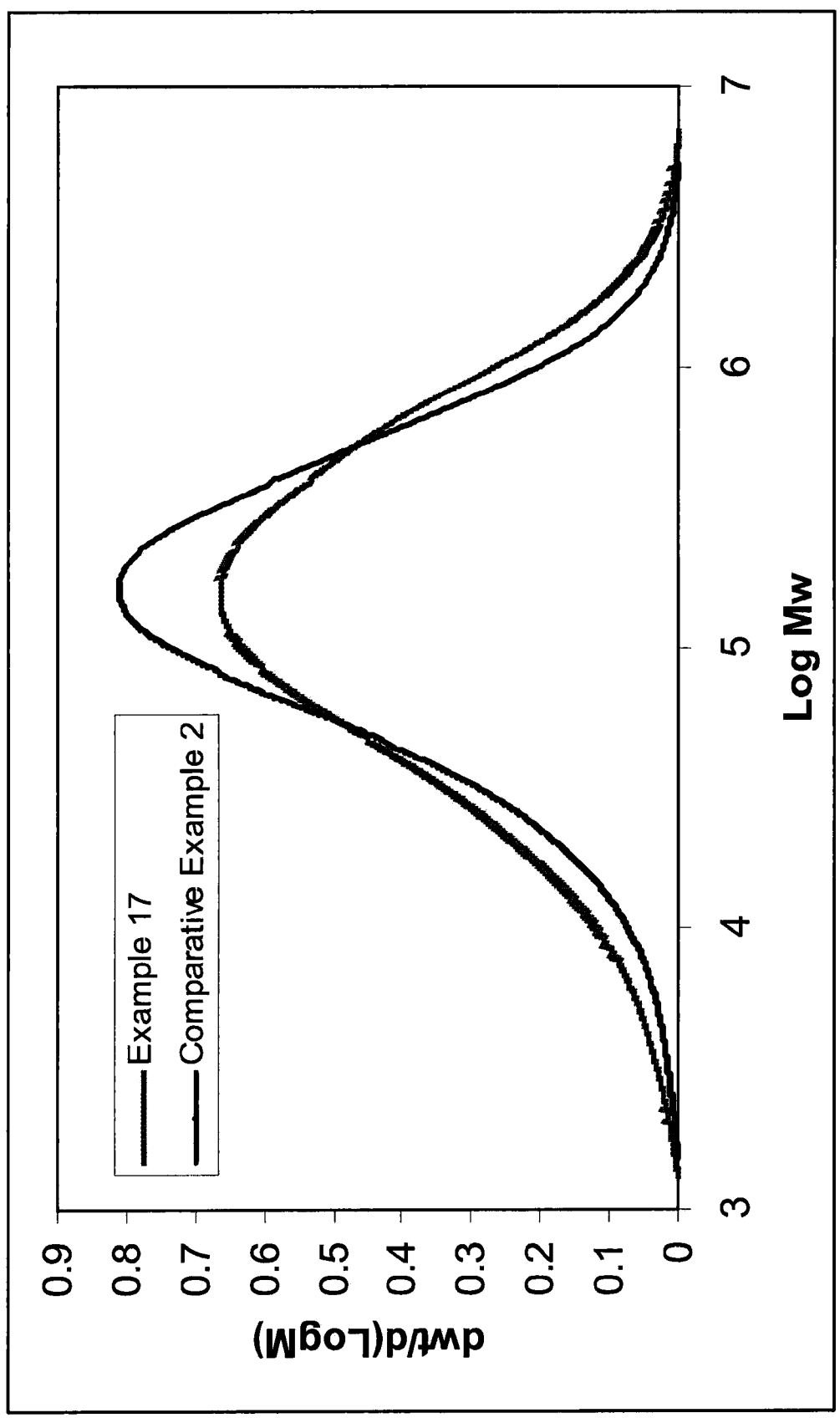
FIG. 4 shows the GPC chromatographs of products obtained in accordance with the procedures of Example 17 and Comparative Example 2.

The polymer powder obtained in the polymerization was admixed with an additive mixture in the granulation step. Granulation was carried out with addition of additives using a twinscrew extruder ZSK 30 from Werner & Pfleiderer at a melt temperature of 230° C. The polymer composition obtained contained 0.035% by weight of an antioxidant (trade name: Anox 20, from Chemtura Corporation), 0.075% by weight of an antioxidant (trade name: Anox BB021, from Chemtura Corporation) and 0.1% by weight of calcium stearate (from Baerloch USA). The properties of the polymer composition are shown in Table 4 and FIG. 4. The data were determined on the polymer composition after addition of additives and granulation or on test specimens produced therefrom. The activity of catalyst (AC) was also measured and shown in Table 4.

Comparative Example 2

The polymerization was performed in the same manner as in Example 17 except that the hydrogen added was 7.1 liter and the silane 4,9-Di-tert-butyl-1,6-dioxa-4,9-diaza-5-sila-spiro[4.4]nonane was replaced by cyclohexylmethyldimethoxysilane (C-donor). The results are shown in Table 4 and FIG. 4.

TABLE 4

| | Example No. | |
|---|---|---|
| | Ex. 17 | Comp. Ex. 2 |
| Donor | 4,9-Di-tert-butyl-1,6-dioxa-4,9-diaza-5-sila-spiro[4.4]nonane | C-donor |
| Activity (gPP/gCat.) | 24500 | 23000 |
| Mw/Mn | 6.9 | 4.1 |
| MI (g/10 min) | 6.1 | 6.2 |
| Flex Modulus (Kpsi) | 229 | 213 |
| Tensile Strength @ Yield (psi) | 5393 | 5294 |
| Impact Strength (ft lb/in) | 0.6 | 0.5 |

TABLE 4-continued

| | Example No. | |
|---|---|---|
| | Ex. 17 | Comp. Ex. 2 |
| Elongation @ Yield (%) | 8 | 8 |
| Rockwell Hardness | 105 | 105 |
| HDT@66 psi, ° C. | 117.1 | 107.4 |
| Tm (° C.) | 166.1 | 164.0 |
| Crystallization Temp, ° C. | 121.6 | 117.1 |

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. Whenever a numerical range with a lower limit and an upper limit is disclosed, any number falling within the range is specifically disclosed. Moreover, the indefinite articles "a" or "an", as used in the claims, are defined herein to mean one or more than one of the element that it introduces.

What is claimed is:

1. A catalyst system for the polymerization or co-polymerization of alpha-olefin comprising a solid Ziegler-Natta type catalyst component, a co-catalyst component, and an electron donor component comprising at least one cyclic organosilicon compound of the formula:

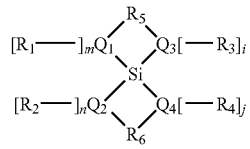

wherein $Q_1$, $Q_2$, $Q_3$ and $Q_4$ are each a hetero-atom independently selected from the group consisting of N, O, S, Si, B, P; wherein $R_1$, $R_2$, $R_3$ and $R_4$ are independently each a hydrocarbon-based substituent to $Q_1$, $Q_2$, $Q_3$ and $Q_4$, respectively; wherein i, j, m, and n are independently 0-3; and wherein $R_5$ and $R_6$ are independently each a bridging group with backbone chain length between their two respective hetero-atoms $Q_1$ and $Q_3$, and $Q_2$ and $Q_4$, respectively, being 1-8 atoms, wherein the backbone of said bridging group is selected from the group consisting of aliphatic, alicyclic and aromatic radicals.

2. A catalyst system according to claim 1, wherein at least one of the bridging groups comprises a $C_1$-$C_{20}$ linear or branched substituent.

3. A catalyst system according to claim 1, wherein one or more of the carbon atoms and hydrogen atoms of $R_1$, $R_2$, $R_3$, $R_4$, $R_5$, or $R_6$ is replaced with a hetero-atom selected from the group consisting of N, O, S, Si, B, P, and halogen atoms.

4. A catalyst system according to claim 1, wherein two or more of said $R_1$, $R_2$, $R_3$, $R_4$, $R_5$, and $R_6$ are linked to form a saturated or unsaturated monocyclic or polycylic ring.

5. A catalyst system according to claim 1, wherein said backbone chain length between two hetero-atoms $Q_1$ and $Q_3$ of the bridging group $R_5$ is from 2 to 4 atoms.

6. A catalyst system according to claim 1, wherein said backbone chain length between two hetero-atoms $Q_2$ and $Q_4$ of the bridging group $R_6$ is from 2 to 4 atoms.

7. A catalyst system according to claim 1, wherein said hetero-atom $Q_1$ in Formula 1 is selected from the group consisting of N, O, Si, and B.

8. A catalyst system according to claim 1, wherein said hetero-atom $Q_2$ in Formula 1 is selected from the group consisting of N, O, Si, and B.

9. A catalyst system according to claim 1, wherein said hetero-atom $Q_3$ Formula 1 is oxygen.

10. A catalyst system according to claim 1, wherein said hetero-atom $Q_3$ Formula 1 is nitrogen.

11. A catalyst system according to claim 1, wherein said hetero-atom $Q_4$ in Formula 1 is oxygen.

12. A catalyst system according to claim 1, wherein said hetero-atom $Q_4$ in Formula 1 is nitrogen.

13. A composition comprising a compound of the formula:

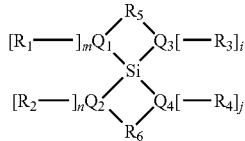

wherein $Q_1$, $Q_2$, $Q_3$, and $Q_4$ are each a hetero-atom independently selected from the group consisting of N, O, S, Si, B, P;
wherein $R_1$, $R_2$, $R_3$, and $R_4$ are independently each a hydrocarbon-based substituent to $Q_1$, $Q_2$, $Q_3$, and $Q_4$, respectively;
wherein i, j, m, and n are independently 0-3; and
wherein $R_5$ and $R_6$ are independently each a bridging group with backbone chain length between their two respective hetero-atoms $Q_1$ and $Q_3$, and $Q_2$ and $Q_4$, respectively, being 1-8 atoms,
wherein the backbone of said bridging group is selected from the group consisting of aliphatic, alicyclic, and aromatic radicals,
wherein one or more of the carbon atoms and hydrogen atoms of $R_1$, $R_2$, $R_3$, $R_4$, $R_5$, or $R_6$ is replaced with a hetero-atom selected from the group consisting of N, O, S, Si, B, P, and halogen atoms.

14. A composition comprising a compound of the formula:

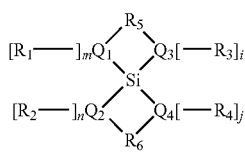

wherein $Q_1$, $Q_2$, $Q_3$, and $Q_4$ are each a hetero-atom independently selected from the group consisting of N, O, S, Si, B, P;
wherein $R_1$, $R_2$, $R_3$, and $R_4$ are independently each a hydrocarbon-based substituent to $Q_1$, $Q_2$, $Q_3$, and $Q_4$, respectively;
wherein i, j, m, and n are independently 0-3; and
wherein $R_5$ and $R_6$ are independently each a bridging group with backbone chain length between their two respective hetero-atoms $Q_1$ and $Q_3$, and $Q_2$ and $Q_4$, respectively, being 1-8 atoms,
wherein the backbone of said bridging group is selected from the group consisting of aliphatic, alicyclic, and aromatic radicals,
wherein two or more of said $R_1$, $R_2$, $R_3$, $R_4$, $R_5$, and $R_6$ are linked to form a saturated or unsaturated monocyclic or polycyclic ring.

15. A composition according to claim 13 or 14, wherein said backbone chain length between two hetero-atoms $Q_1$ and $Q_3$ of the bridging group $R_5$ is from 2 to 4 atoms.

16. A composition according to claim 13 or 14, wherein said backbone chain length between two hetero-atoms $Q_2$ and $Q_4$ of the bridging group $R_6$ is from 2 to 4 atoms.

17. A method for polymerizing an alpha-olefin comprising polymerizing alpha-olefin in the presence of a solid Ziegler-Natta type catalyst component, a co-catalyst component, and an electron donor component comprising at least one cyclic organosilicon compound of the formula:

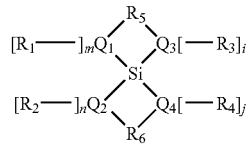

wherein $Q_1$, $Q_2$, $Q_3$ and $Q_4$ are each a hetero-atom independently selected from the group consisting of N, O, S, Si, B, P;
wherein $R_1$, $R_2$, $R_3$ and $R_4$ are independently each a hydrocarbon-based substituent to $Q_1$, $Q_2$, $Q_3$ and $Q_4$, respectively;
wherein i, j, m, and n are independently 0-3; and
wherein $R_5$ and $R_6$ are independently each a bridging group with backbone chain length between their two respective hetero-atoms $Q_1$ and $Q_3$, and $Q_2$ and $Q_4$, respectively, being 1-8 atoms,
wherein the backbone of said bridging group is selected from the group consisting of aliphatic, alicyclic and aromatic radicals.

18. A method according to claim 17, wherein one or more of the carbon atoms and hydrogen atoms of $R_1$, $R_2$, $R_3$ $R_4$, $R_5$, or $R_6$ is replaced with a hetero-atom selected from the group consisting of N, O, S, Si, B, P, and halogen atoms.

19. A method according to claim 17, wherein two or more of said $R_1$, $R_2$, $R_3$, $R_4$, $R_5$, and $R_6$ are linked to form a saturated or unsaturated monocyclic or polycylic ring.

20. A method according to claim 17, wherein said backbone chain length between two hetero-atoms $Q_1$ and $Q_3$ of the bridging group Rs is from 2 to 4 atoms.

21. A method according to claim 17, wherein said backbone chain length between two hetero-atoms $Q_2$ and $Q_4$ of the bridging group $R_6$ is from 2 to 4 atoms.

\* \* \* \* \*

UNITED STATES PATENT AND TRADEMARK OFFICE
CERTIFICATE OF CORRECTION

PATENT NO. : 7,790,819 B1　　　　　　　　　　　　　　　　　　　　　　　　　　Page 1 of 1
APPLICATION NO. : 12/422705
DATED : September 7, 2010
INVENTOR(S) : Fang et al.

It is certified that error appears in the above-identified patent and that said Letters Patent is hereby corrected as shown below:

Title page, Item (57), Abstract,
Line 6 below the formula:　　　　　after "0 to 3" insert --0 to 3.--

Claim 20:
Column 16, Line 58:　　　　　　　　delete "Rs" and replace with --$R_5$--

Signed and Sealed this

Twenty-sixth Day of October, 2010

David J. Kappos
*Director of the United States Patent and Trademark Office*